United States Patent [19]

Unger et al.

[11] Patent Number: 5,628,327
[45] Date of Patent: May 13, 1997

US005628327A

[54] APPARATUS FOR PERFORMING BIOPSIES AND THE LIKE

[75] Inventors: Evan Unger; Frederick S. Pereles, both of Tucson, Ariz.

[73] Assignee: ImaRx Pharmaceutical Corp., Tucson, Ariz.

[21] Appl. No.: 356,150

[22] Filed: Dec. 15, 1994

[51] Int. Cl.$^6$ .................................................. A61B 10/00
[52] U.S. Cl. ........................................................... 128/749
[58] Field of Search ........................... 128/749–754, 128/665, 653.1, 664, 662.05; 606/130

[56] References Cited

U.S. PATENT DOCUMENTS

| | | | |
|---|---|---|---|
| 4,296,329 | 10/1981 | Mirabella | 250/491 |
| 4,341,220 | 7/1982 | Perry | 128/630 |
| 4,385,397 | 5/1983 | Verro | 378/20 |
| 4,583,538 | 4/1986 | Onik et al. | 128/303 B |
| 4,592,352 | 6/1986 | Patil | 128/303 B |
| 4,651,732 | 3/1987 | Frederick | 128/303 R |
| 4,733,661 | 3/1988 | Palestrant | 128/303 B |
| 4,930,525 | 6/1990 | Palestrant | 128/898 |
| 5,031,203 | 7/1991 | Trecha | 378/205 |
| 5,047,036 | 9/1991 | Koutrouvelis | 606/130 |
| 5,316,014 | 5/1994 | Livingston | 128/754 |
| 5,320,111 | 6/1994 | Livingston | 128/754 |
| 5,494,034 | 2/1996 | Schlondorff et al. | 128/653.1 |
| 5,497,265 | 3/1996 | Ishikawa et al. | 359/390 |

OTHER PUBLICATIONS

Frederick, et al., "A Light–guidance System To Be Used for CT–guided Biopsy", Radiology, 1985.

Nagata, et al., "Laser Projection System for Radiotherapy and CT–Guided Biopsy", Technical Note, *Journal of Computer Assisted Tomography*, pp. 1046–1048, Nov./Dec. 1990.

Nishidai, et al., "CT Simulator: A New 3–D Planning and Simulating System for Radiotherapy: Part 1, Description of System", *I.J. Radiation Oncology Biol. Phys.*, vol. 18 No. 3, pp. 499–504, Mar. 1990.

Nagata, et al., "CT Simulator: A New 3–D Planning and Simulating System for Radiotherapy: Part 2, Clinical Application", *I.J. Radiation Oncology Biol. Phys.*, vol. 18 No. 3, pp. 505–513, Mar. 1990.

Wunschik, et al., "Stereoactic Biopsy Using Computed Tomography", *Journal of Computer Assisted Tomography*, vol. 8, No. 1, pp. 32–37, Feb. 1984.

Onik, et al., "CT Body Stereotaxis: An Acid for CT–Guided Biopsies", *AJR* 146, pp. 163–168, Jan. 1986.

Onik, et al., "CT–guided Aspirations for the Body: Comparison of Hand Guidance with Stereotaxis", *Radiology* vol. 166 No. 2 pp. 389–394, Feb. 1988.

Drummond, et al., "Deflection of spinal needles by the bevel", *Anaesthesia*, vol. 35, pp. 854–857, 1980.

*Primary Examiner*—Sam Rimell
*Assistant Examiner*—Pamela L. Wingood
*Attorney, Agent, or Firm*—Woodcock Washburn Kurtz Mackiewicz & Norris

[57] ABSTRACT

A device for directing and supporting a laser during laser guided biopsies. The device comprises a track attached to a computed tomography table. A vertically extending post is slidably mounted on the track so that the post can be moved parallel to the axis of the table. A rail is slidably mounted on the post and extends across the width of the table. A first bracket is slidably mounted on the rail and a first rotary stage is attached to the bracket that allows rotation in one vertical plane. A second bracket is attached to the first rotary stage. A second rotary stage that allows rotation in a second vertical plane, which is perpendicular to the first vertical plane, is attached to the second bracket. A laser is mounted on the second rotary stage, thereby allowing the laser's beam to be set at a compound angle by rotation of the two rotary stages.

18 Claims, 15 Drawing Sheets

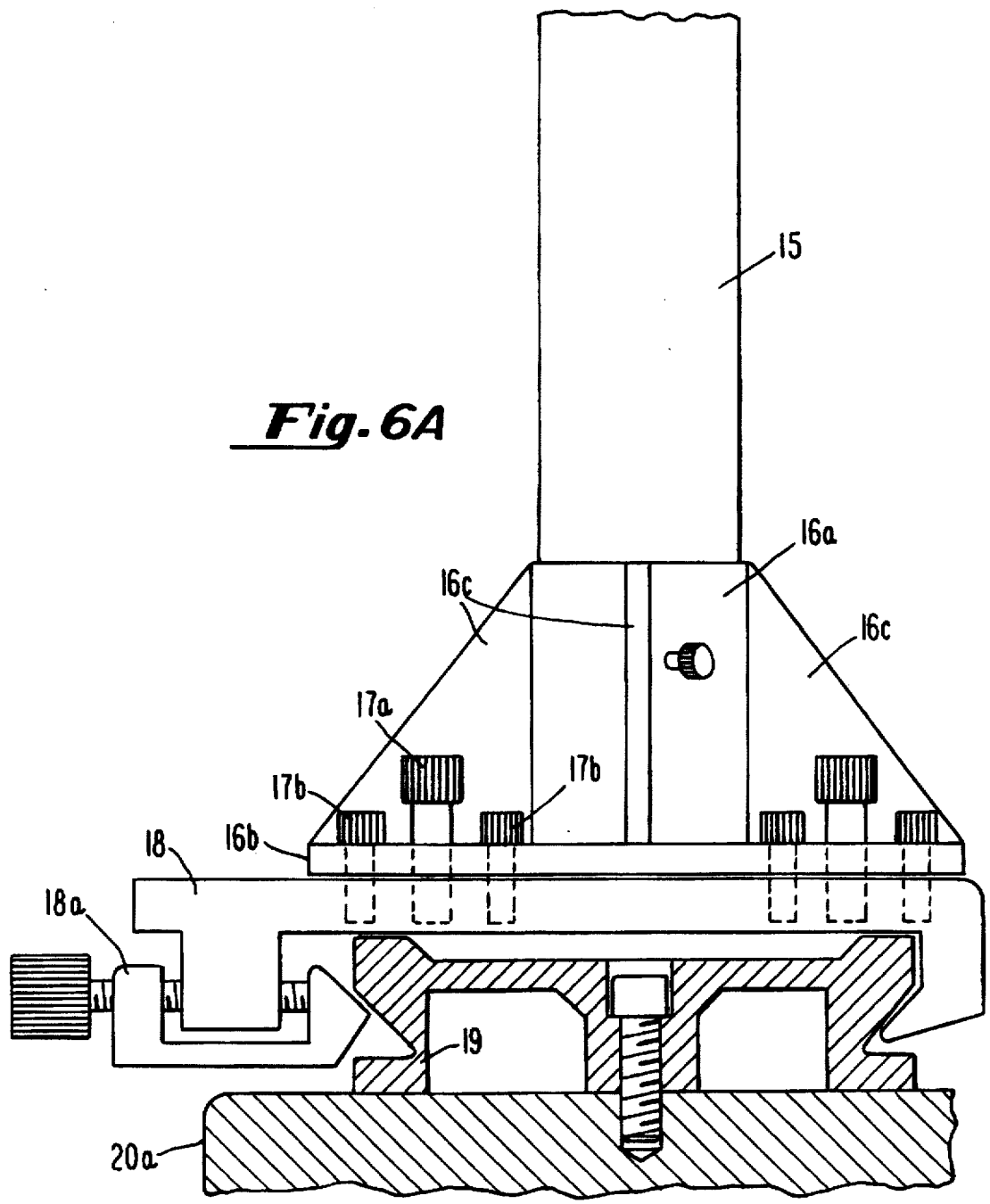

5,628,327

APPARATUS FOR PERFORMING BIOPSIES AND THE LIKE

FIELD OF THE INVENTION

The current invention is directed to an apparatus for performing biopsies and other similar procedures in which a probe is inserted into a patient's body. More specifically, the current invention is directed to an apparatus that includes a device for supporting and aiming a laser beam used to guide the probe during its insertion into the body and a probe that facilitates the use of the laser beam as a guide. The apparatus is especially useful in conjunction with Computed Tomography (CT) and Magnetic Resonance Imaging (MRI) techniques.

BACKGROUND OF THE INVENTION

Imaging techniques such as computed tomography are often used to aid in directing the insertion of one or more probes into the patient's body during percutaneous biopsies and other similar procedures (e.g., hyperthermia probes, radiation seeds, etc.). In CT aided biopsies, a scan is typically obtained to visualize the lesion to be biopsied. Using the image generated during the scan, the target site and the entry point on the patient's skin are selected and marked on the CRT screen. The computer then calculates the distance and the angle of the insertion in order to reach the target site and displays the biopsy path on the screen.

The entry point is then marked on the patient's skin and the needle or probe is advanced into the patient's skin and tissues under free-hand control by the physician. Because of anatomy and overlying structures, the path selected for entry of the needle or probe is often not vertical but rather at an angle to the vertical. Often times a compound angle—that is, an angle with respect to the vertical in both the sagittal plane (i.e., the plane extending from head to toe) and the axial plane (i.e., the plane extending across the body from one side to the other)—must be used in order to avoid penetrating areas such as vital organs.

Although such procedures may be performed using a free-hand technique, it is difficult to ensure sufficient accuracy in orienting and maintaining the needle at the correct angle. The free-hand technique is even less precise and even more difficult when a compound angle is used. For example, in deep biopsies, even a few degrees deviation in angulation will result in a significant error in needle position. This can have undesirable consequences when the target lesion (e.g., tumor) is small and the path is close to surrounding vital structures, such as the aorta and nerves.

One approach taken in the past to increase the accuracy of needle orientation is the use of device to physically constrain the needle so that its path conforms to the predetermined path, for example, such as that used in stereotaxis guidance systems. One such device is disclosed in U.S. Pat. No. 4,583,538 (Onik et al.). Unfortunately, this approach has several drawbacks. First, since the guidance device touches the needle, it must be sterilized prior to use. Second, and perhaps more importantly, the physician loses some degree of control and feel over the needle placement. The tactile sensation of the user is an essential element in the control of needle placement. Guides which physically constrain the needle necessarily compromise tactile needle control by the user. Lastly, setting the desired angulation is often a difficult and time consuming process in such devices and involves making various complex calculations.

Another approach involves the use of a light beam or laser as a guide so that the needle is not touched or physically constrained. In one such approach, two intersecting beams of light are used to guide the needle placement, see, for example, U.S. Pat. No. 4,651,732 (Frederick). Unfortunately, such systems required two light sources and, thereby, increase the complexity of the device and its use. In another approach, a computer and a raster driven light source connected to a C-arm are used to generate a laser beam onto the patient, see, for example, Nagata et al., "Laser Projection System for Radiotherapy and CT-Guided Biopsy," Journal of Computer Assisted Tomography, vol. 14, no. 6, p. 1046–1048 (1990). However, such systems are quite complex and, accordingly, expensive and have not entered into routine clinical practice for biopsies. In addition, the characteristics of such devices may limit the range of compound angles. Also, its physical mass can be in the way in certain biopsy situations.

Further, probes for use in biopsies typically employ a stylet that slides within a hollow needle. In order to force the stylet into the tissue and guide its path, the needle must be firmly grasped along its length. However, such grasping can cause the probe to deflect. Although enlarged hubs have been developed that allow the needle to be more firmly grasped, one must typically insert a finger over the rear end of the stylet in order to prevent its tip from retracting into the needle, thereby complicating the guiding and insertion of the stylet.

Consequently, it would be desirable to provide an apparatus for performing biopsies and the like using a free-hand technique, with a light beam as a guide, capable of accurately and firmly directing the beam at an angle and yet that is easy to use and readily adjustable over a wide range of angles. It would be further desirable to provide a probe that facilitated such a light beam guided, free-hand technique.

SUMMARY OF THE INVENTION

It is an object of the current invention to provide an apparatus for performing biopsies and the like using a free-hand technique, with a light beam as a guide, capable of accurately and firmly directing the beam at an angle and yet that is easy to use and readily adjustable over a wide range of angles. This and other objects is accomplished in an apparatus for performing light beam guided penetrations of a patient's body, comprising (i) a surface for supporting a patient's body, (ii) a track extending along said surface in a first direction, (iii) a vertically extending post slidably mounted on said track for movement therealong in said first direction, (iv) a rail projecting from said post in a second direction perpendicular to said first direction, (v) a support structure slidably mounted on said rail for movement therealong in said second direction, a first rotatable mount coupled to said support structure and a second rotatable mount coupled to said first rotatable mount, said first and second rotatable mounts oriented so as to provide rotation within first and second perpendicularly oriented vertically extending planes, respectively, and (vi) a light source couple to said second rotatable mount for projecting a beam of light onto said patient.

In one embodiment of the invention, the apparatus includes a probe comprised of a stylet and a needle. The needle has a flanged end and the stylet has a locking mechanism for locking it in place on the needle.

BRIEF DESCRIPTION OF THE DRAWINGS

FIGS. 6A and 6B are end and plan views, respectively, of the portion of the device shown in FIG. 1B where the vertical support post assembly mates with the track.

DESCRIPTION OF THE PREFERRED EMBODIMENT

Figure 1A:
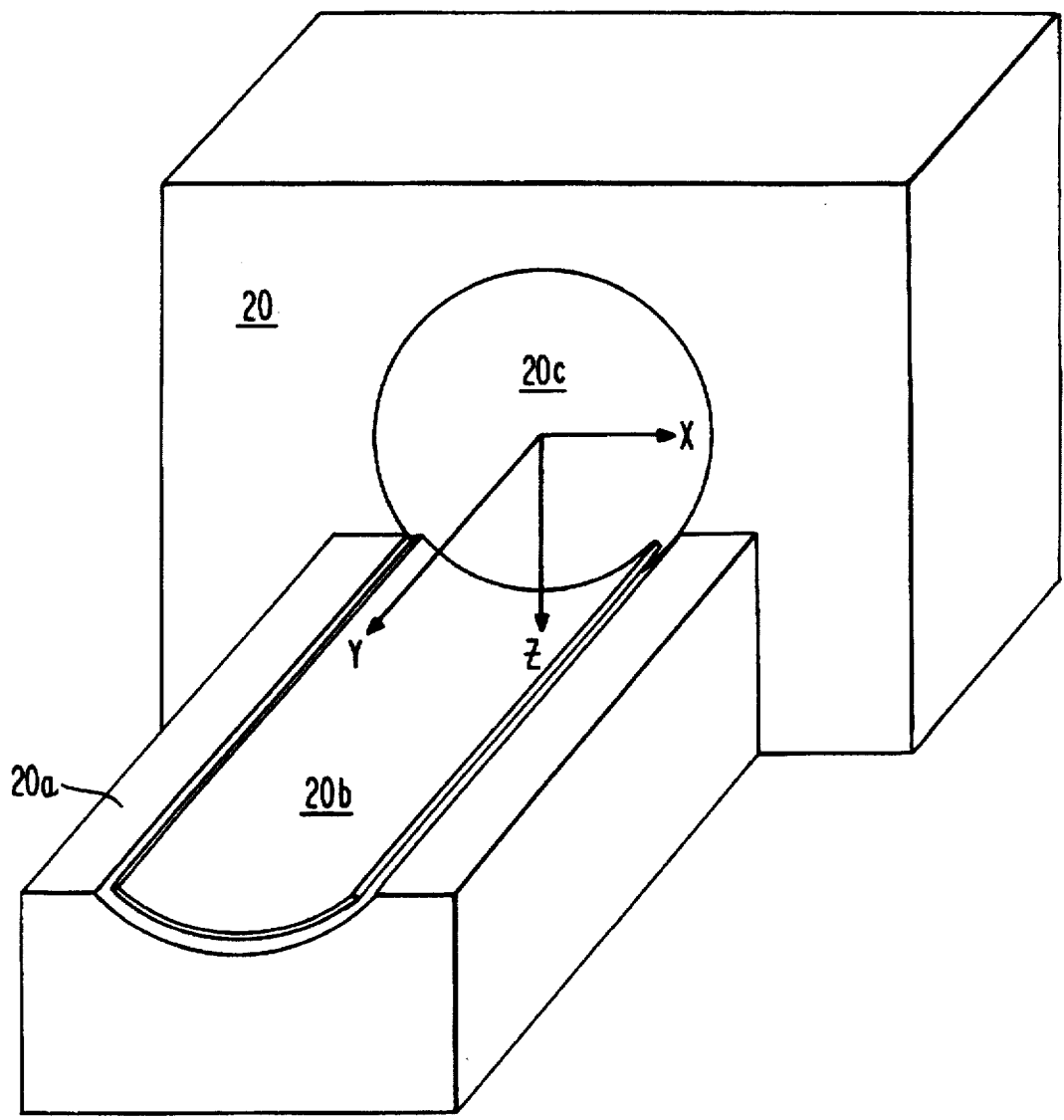
FIG. 1A is an isometric view showing a CT scanning system according to the prior art.

There is shown in FIG. 1A a CT scanning system according to the prior art. The system includes a CT machine 20, a CT table 20a, a CT couch 20b and a gantry 20c. A Cartesian coordinate system is shown, with the z-direction being vertical, the x-direction being transverse to the body of a patient lying on the couch 20b, and the y-direction extending longitudinally along the patient from head to toe. Thus, the x-z plane defines an axial plane and the y-z plane defines a sagital plane.

Figure 1B:
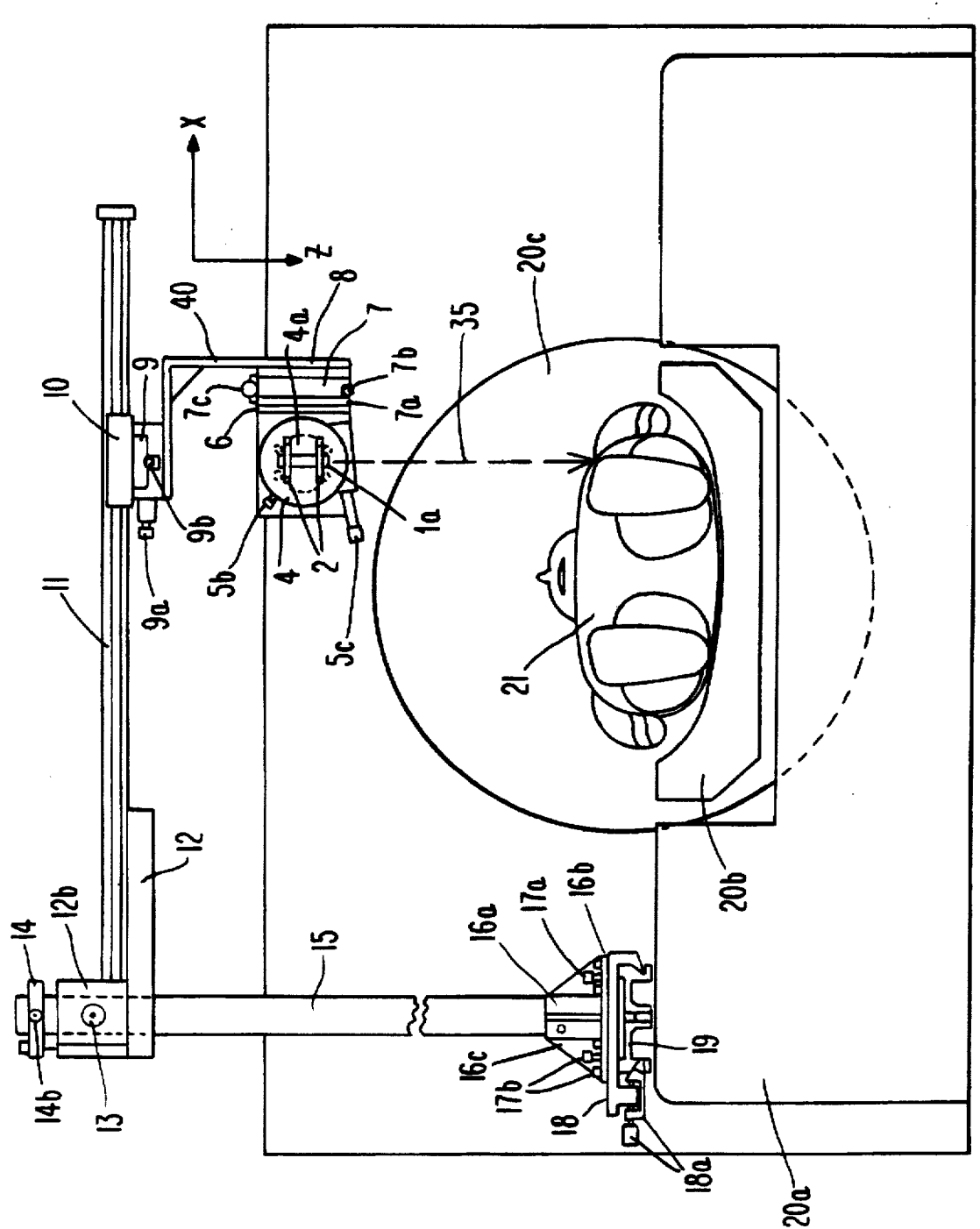
FIG. 1B is an end view of the beam supporting and directing device according to the current invention mounted on the side of the CT table.

One embodiment of the apparatus for supporting and directing a light beam in order to guide the path of a biopsy probe, according to the current invention, as installed on the side of the CT table 20a, is shown in FIG. 1B. The device comprises a y-direction track 19 attached to the CT table 20a, a vertical support post 15 slidable mounted on the track 19, an x-direction rail 11 slidably mounted on the vertical support post, and a laser beam supporting structure 40 slidably mounted on the rail 11. A laser 1a installed on support structure 40 generates a beam of light 35 aimed at a patient 21 that can be used to guide the path of a biopsy probe, as discussed further below.

Figure 2A:
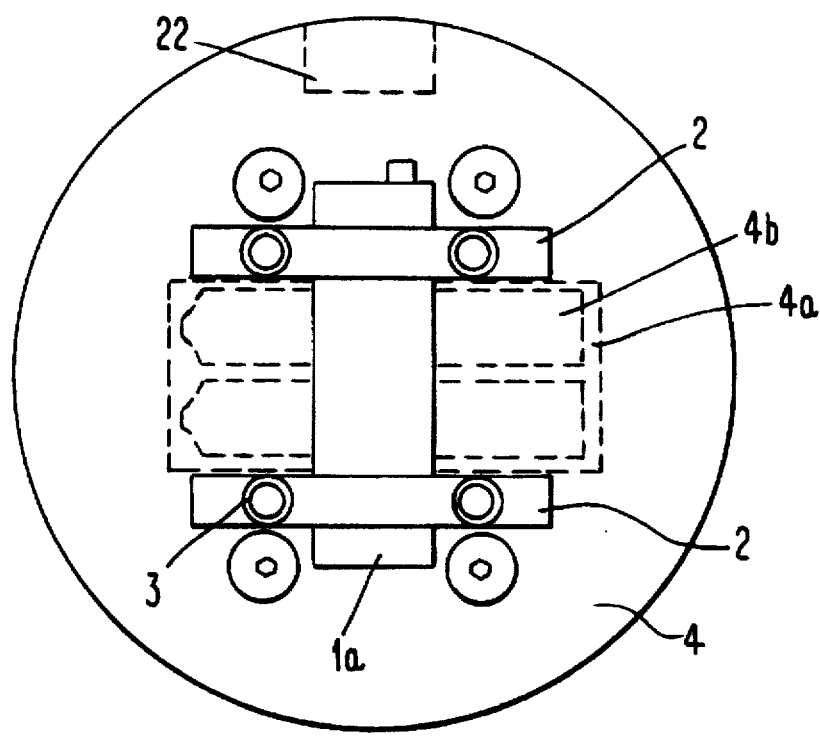
FIGS. 2A and 2B are plan and elevation views, respectively, of the laser mounting block assembly of the device shown in FIG. 1B.
Figure 2B:
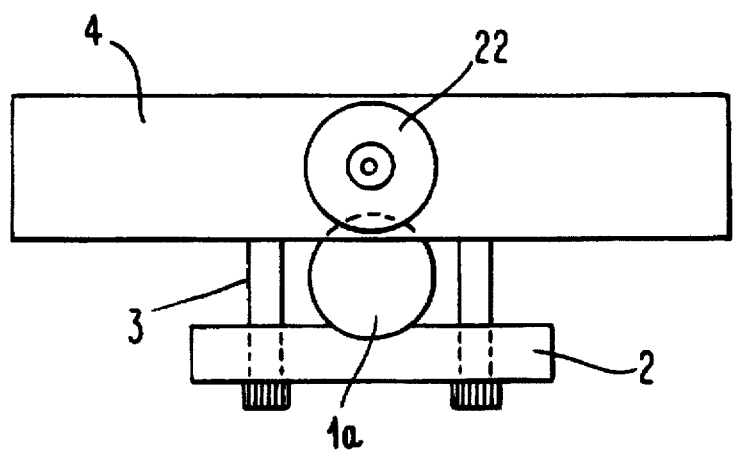

As shown in FIGS. 2A and 2B, the laser 1a, which may be of the helium neon diode type, is secured within a groove formed in a plastic mounting block 4, such as a delrin block, using two tie down bars 2 that are attached to the mounting block 4 by screws 3. This arrangement ensures that the laser 1b will maintain its orientation with respect to the mounting block 4. Suitable lasers include model CPM 01-670-A-C available from Power Technology Inc. of Little Rock, Ark. The laser 1a is preferably certified by the Center for Devices and Radiologic Health (CDRH) and is, therefore, pre-approved by the FDA/CDRH for end product use as long as the laser module is not enclosed or otherwise inaccessible, and warning labels are not removed or modified. Preferably, the laser 1a is apertured for an ultrafine beam spot, which cuts actual laser output to less than 0.5 mW, alleviating the need for any eye protection.

The laser 1a may be powered by any source between two and ten volts (e.g., 2×AAAA batteries or one nine-volt transistor battery.) A shown in FIG. 2A, the laser 1a preferably is powered by two AAA alkaline, standard commercial batteries 4b installed in a battery compartment 4a formed in mounting block 4.

According to an important aspect of the current invention, a level indicating device 22, such as a bullseye leveling bubble, is incorporated into the mounting block 4. The leveling indicating device 22 allows the user to verify that the laser is oriented in the dead vertical position (i.e., a 0° angle with respect to the z-direction in both the x-z and y-z planes) before setting the beam angle based on the CT image. As a result of closely coupling the level indicating device 22 to the laser 1a, by securing both directly onto the same mounting block 4, the user can ensure that the beam angle set on the rotary stages, discussed below, will accurately reflect the angle of the laser with respect to the z-direction in both the x-z and y-z planes.

Figure 3A:
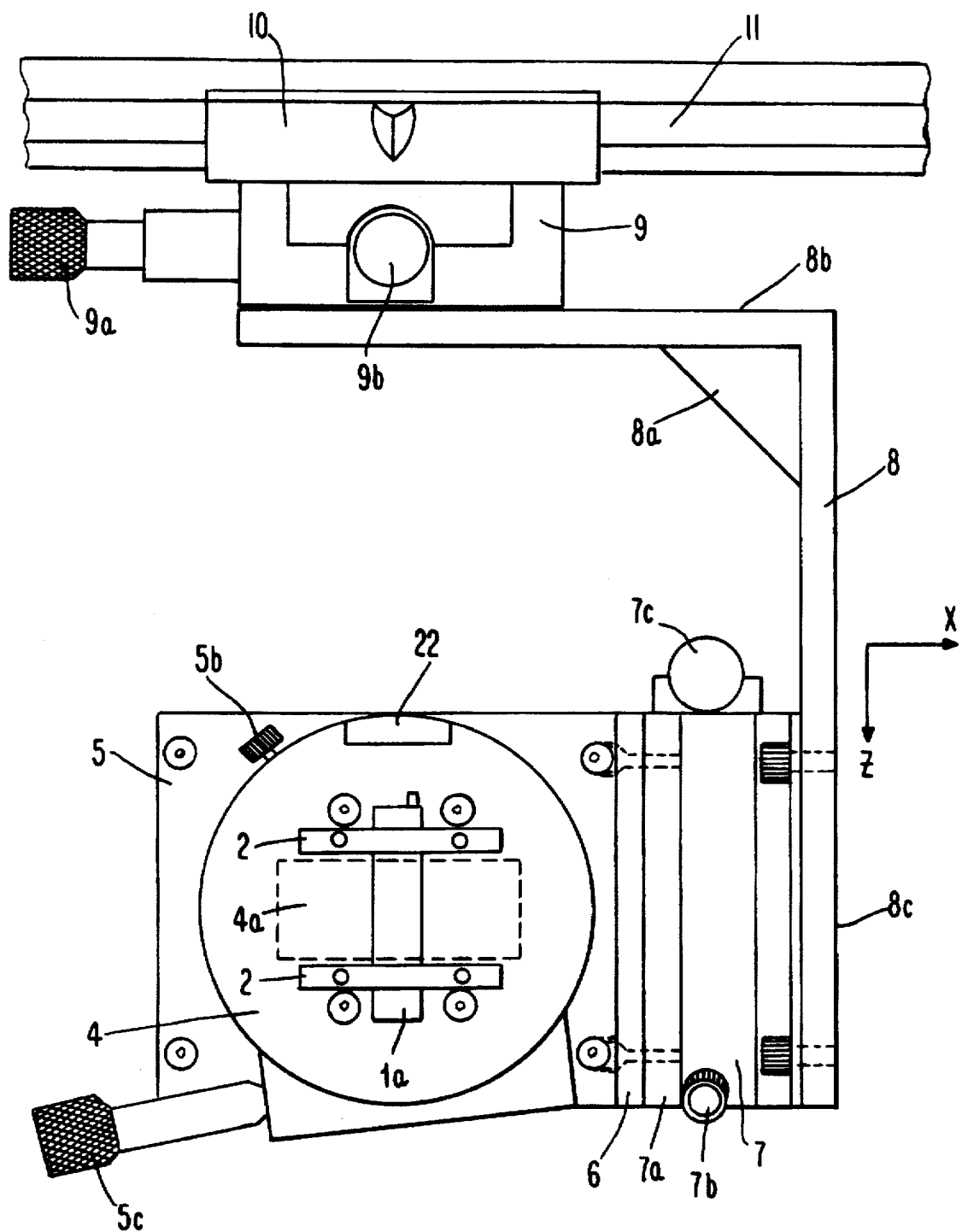
FIGS. 3A and 3B are end views and side views, respectively, of the laser mounting block support structure of the device shown in FIG. 1B.
Figure 3B:
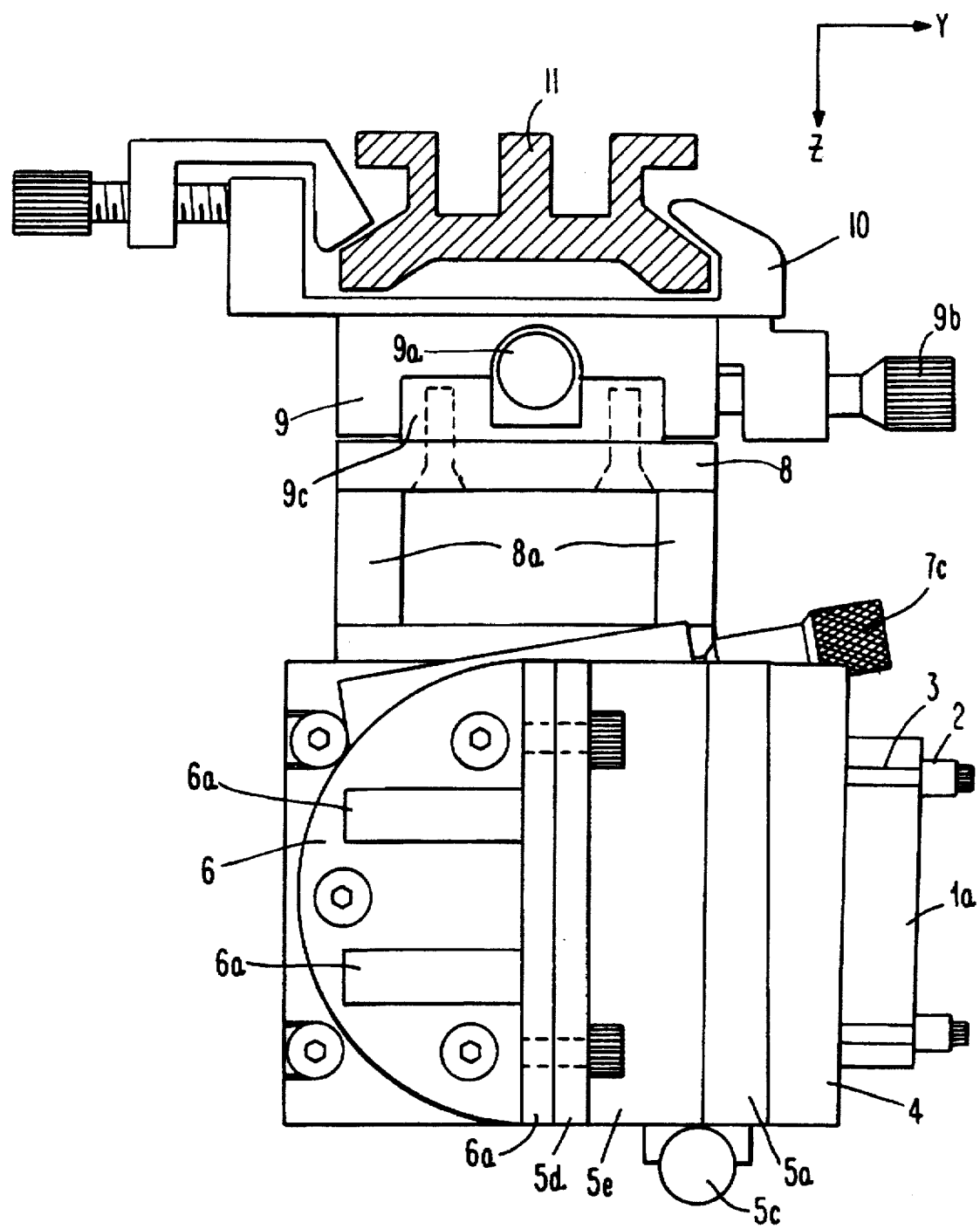
Figure 4:
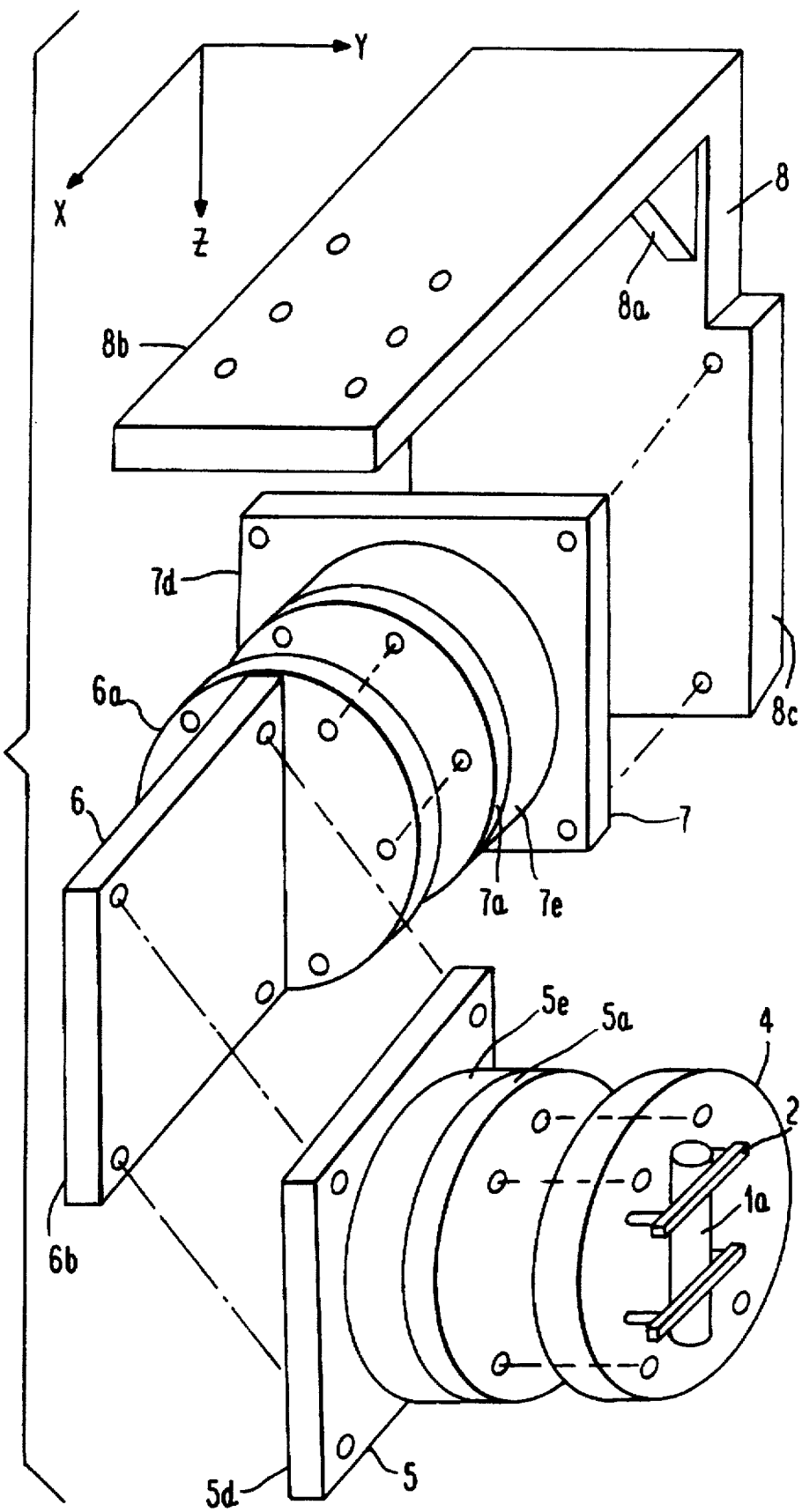
FIG. 4 is an exploded view, partially schematic, of the laser mounting block support structure shown in FIGS. 3A and 3B.

As shown in FIGS. 3A, 3B and 4, the laser supporting structure 40 includes two rotary stages 5 and 7 oriented perpendicularly to each other. Each rotary stage 5 and 7 is comprised of a mounting plate 5d and 7d, a fixed ring 5e and 7e, a rotable ring 5a and 7a coupled to the fixed ring, a locking screw 5b and 7b, and a fine adjustment caliper 5c and 7c. A suitable rotary stage is model M-481-A, available from Newport Corp. of Irvine, Calif.

The rotary stages 5 and 7 are fixed at a right angle with respect to each other by aluminum brackets 6 and 8. The bracket 6 is approximately T-shaped and is comprised of a circular base plate 6a and a rectangular support plate 6b. Gussets 6a may be installed between the plates 6a and 6b to ensure that the bracket 6 remains rigid. The bracket 8 is approximately L-shaped and is comprised of a base plate 8b, a support plate 8c and two gussets 8a installed between the two plates 8b and 8c that ensure that the bracket 8 remains rigid.

As shown best in FIG. 4, the laser mounting block 4 is itself mounted on the rotable ring 5a of the rotary stage 5. The base plate 5d of the rotary stage 5 is secured to the support plate 6b of the bracket 6. The base plate 6a of the bracket 6 is secured to the rotable ring 7a of the rotary stage 7. The base plate 7e of the rotary stage 7 is secured to the support plate 8c of the bracket 8.

The rotary stages 5 and 7 allow adjustment of the beam angle in the two perpendicular vertical planes. The rotary stage 5 allows adjustment of the laser beam 35 angle within the x-z plane, while the rotary stage 7 allows adjustment of the laser beam angle within the y-z plane. Thus, by properly adjusting the rotary stages 5 and 7, the laser beam 35 can be set to a compound angle with respect to the z-direction. Alternatively, if an angle is required in only the y-z plane (i.e., the axial plane), the rotary stage 5 can be set to 0°.

As shown in FIGS. 3A and 3B, the bracket 8 is suspended from a bi-directional translational stage 9. The translational stage 9 comprises a support plate 9c to which the base plate 8b of the bracket 8 is attached and that is slidably mounted within the translational stage 9 so as to be free to move in both the x and y directions. A caliper 9b moves the support plate 9c in the y direction and a caliper 9a moves the support plate 9c in the x direction. A suitable translational stage is model 460A-XY available from Newport Corp. The translational stage 9 permits fine translational adjustment in the x and y directions in a horizontal plane.

The translational stage 9 is attached to an optical rail carrier 10. A suitable rail carrier is model 07 OCN 503 available from Melles Griot of Irvine, Calif. The carrier 10 is free to move along a rigid horizontal rail 11 that extends perpendicularly to the track 19 and from which the carrier is suspended. A suitable rail is model 07 ORN 005 available from Melles Griot. Preferably, rail 11 has a metric ruled side with millimeter markings for translational distance adjustment. Movement along the arm 11 provides rapid gross adjustment in the x direction when the horizontal rail 11 is perpendicular to the CT table 20a.

Figure 5A:
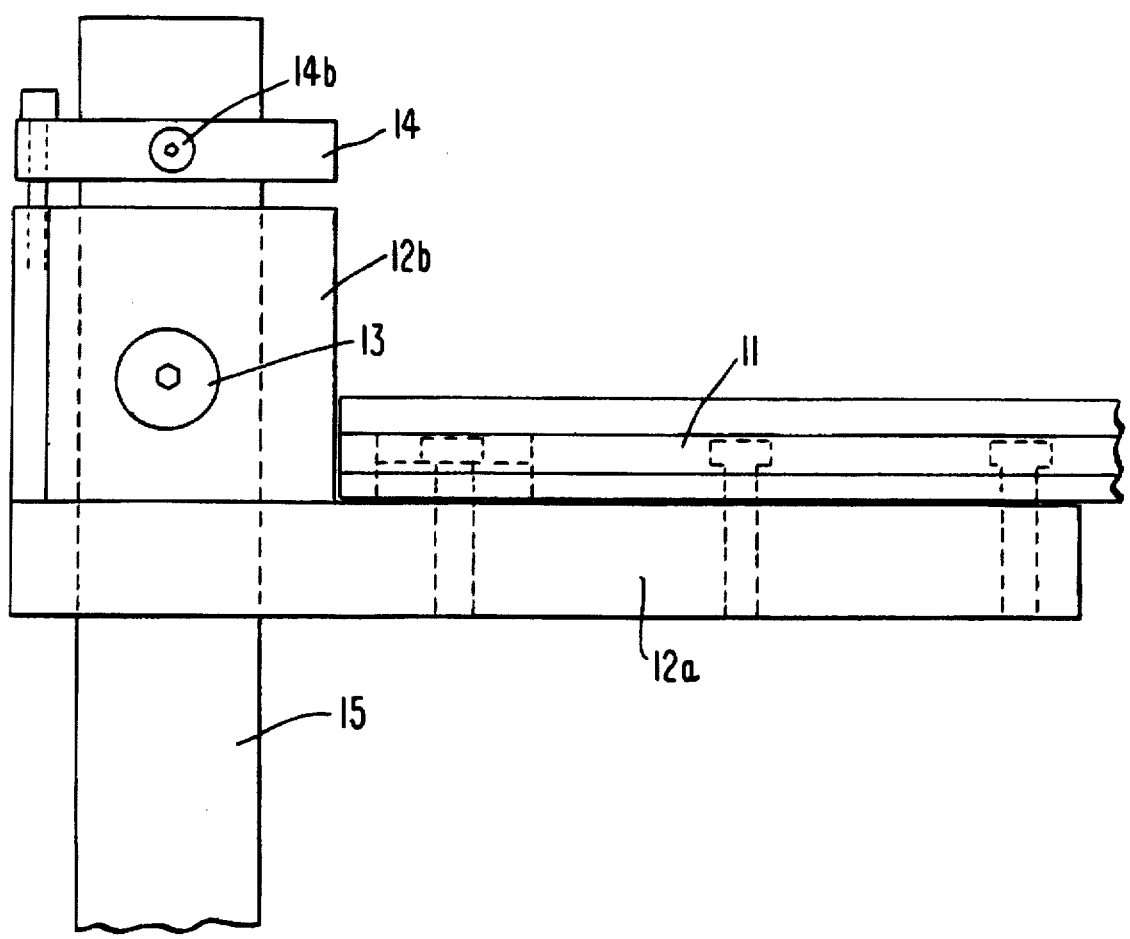
FIGS. 5A and 5B are elevation and plan views, respectively, of the portion of the device shown in FIG. 1B where the horizontal rail support arm clamps to the vertical support post.
Figure 5B:
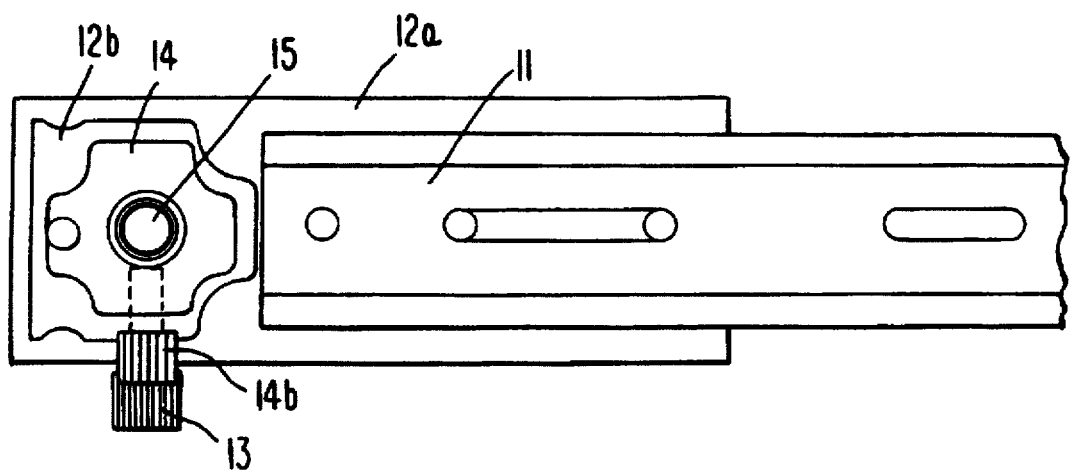

As shown in FIGS. 5A and 5B, the horizontal rail 11 is mounted by a rigid right angle clamp 12 that clamps to the vertical support post 15. The clamp 12 is comprised of a vertical post clamp 12b, an extension plate 12a, and a locking screw 13. A suitable clamp is model M-300-P available from Newport Corp. The platform clamp 12 is used to raise and lower the horizontal rail 11 rapidly, and is preferably equipped with a fine adjustment vertical positioner 14 and locking screw 14b, available from Newport Corp. (model M-32-A). The platform 12 clamp is also capable of rotating the arm in a horizontal plane for versatility and ease of biopsy approach. The platform clamp 12 also serves to hold the horizontal arm 11 rigid and level.

Figure 6B:
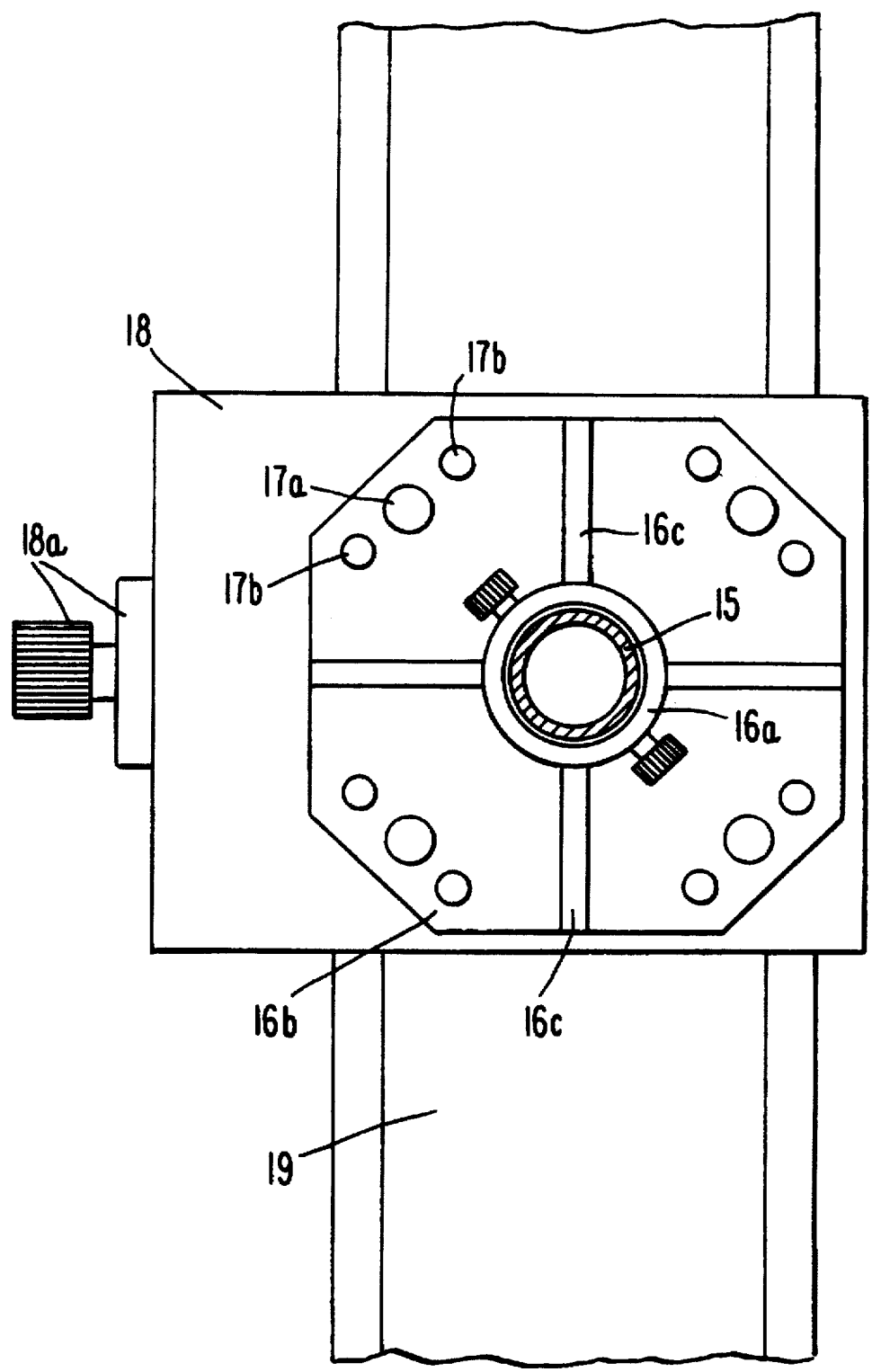

As shown in FIGS. 6A and 6B, the vertical support post 15, to which the horizontal arm 11 is clamped, is slidably mounted to the track 19 installed along the side of the CT table 20a. A suitable track is model 07 ORP 011 available from Melles Griot. The vertical post 15 is mounted via a sleeved collar system 16 to a rail carrier 18 that moves along the track 19. This arrangement enables rapid gross translational movement in the Y direction. The rail carrier 18 position is set on the track 19 by a locking mechanism 18a.

The sleeved collar system 16 comprises a collar 16a, a tilt plate 16b and stiffening gussets 16c. The tilt plate 16b is secured to the rail carrier 18 by tie down screws 17b. Adjusting screws 17a adjust the orientation of the tilt plate 16b so as to allow the vertical post 15 to be adjusted with respect to the vertical, thereby ensuring that the horizontal rail 11 is level.

Figure 7A:
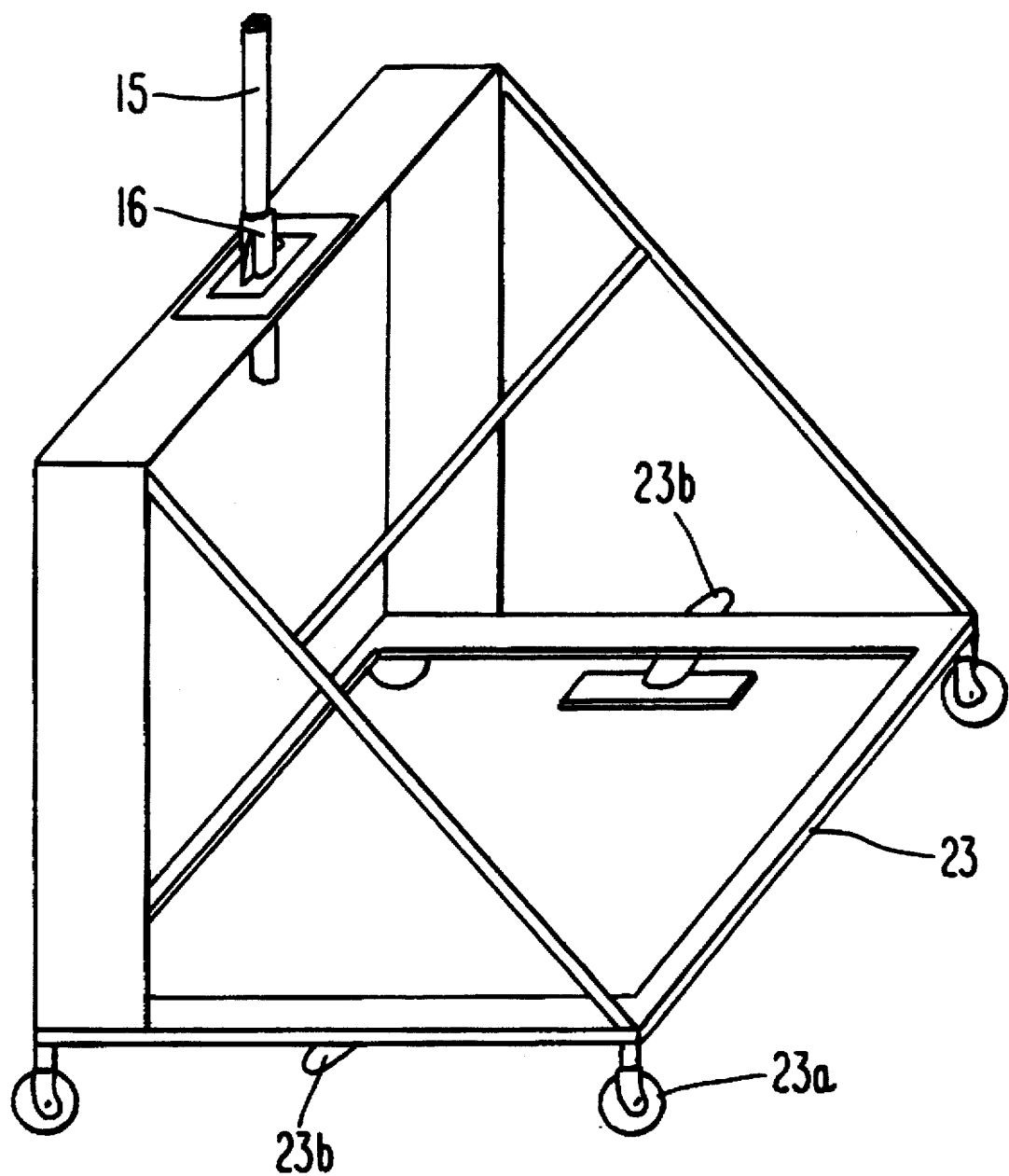
FIGS. 7A and 7B are isometric and elevations views, respectively, of the movable support stand according to another embodiment of the current invention, with FIG. 7B showing the addition of a spacer plate.

According to another embodiment of the current invention, the device may be mounted on a portable floor stand 23, shown in FIG. 7A, rather than attached to the CT table 20a. In this embodiment, the vertical post 15 is mounted directly to the portable floor stand 23 using the sleeved collar system 16 shown in FIGS. 6A and 6B. When the portable floor stand 23 is used, the vertical post 15 may be positioned by moving the floor stand 23 to the desired position adjacent the CT table 20a. When the stand 23 is in the proper position, it is clamped into the locked position via locking swivel casters 23a, such as those available from Darcor Inc. of Brea, Calif. (model OU-BC5-XSRB) or a cooperative floor jack system 23b so that it can no longer move during the procedure unless repositioning is desired. The portable floor stand 23 can be positioned anywhere along the CT table on either side or even at either end of the CT table if needed, thereby providing maximum flexibility.

Figure 7B:
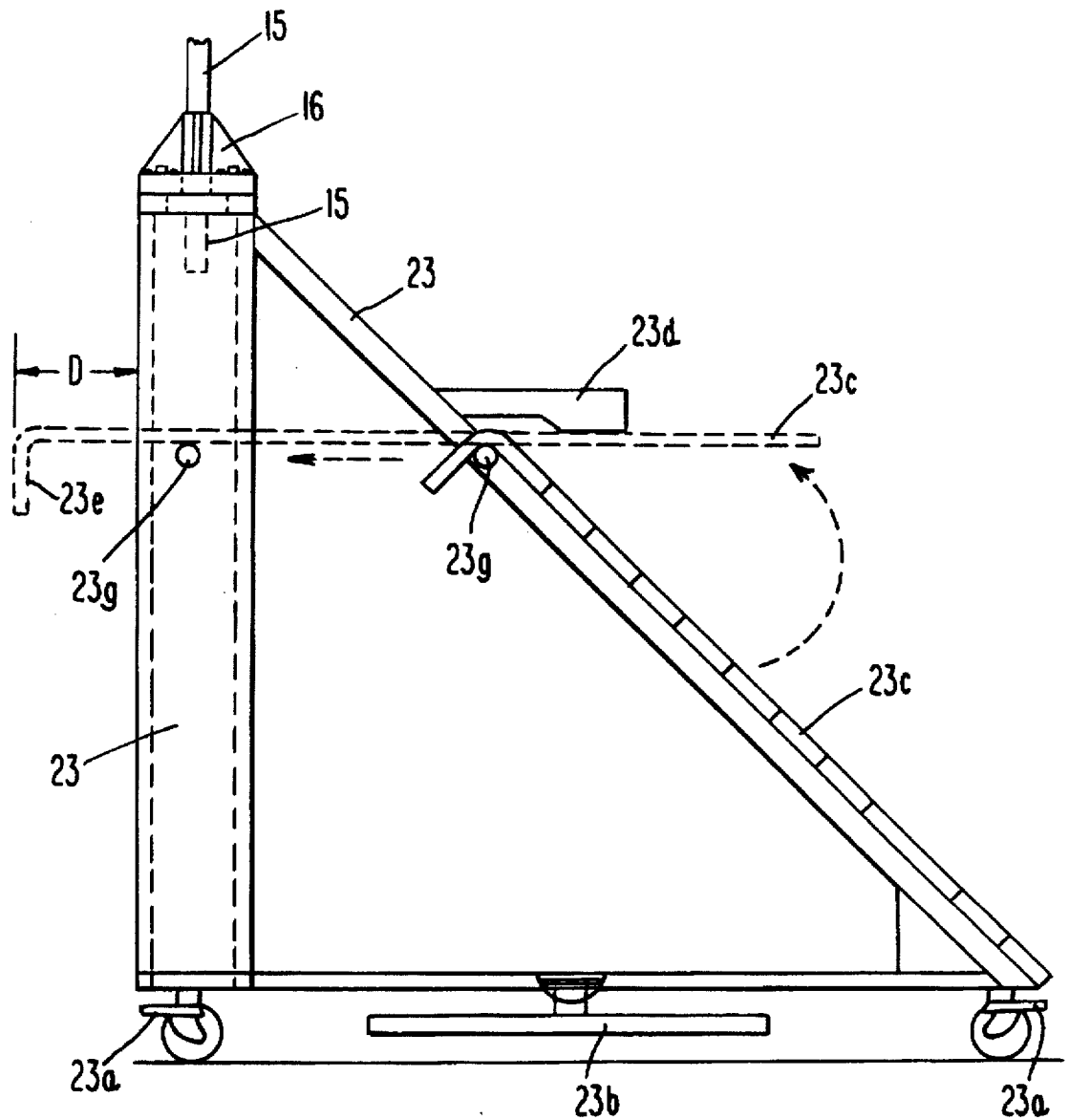

In the embodiment shown in FIG. 7B, an adjustable spacer plate 23c is incorporated into the floor stand 23. When the spacer plate 23c is rotated upward and supported on rests 23g, it is locked in an extended position, shown dotted in FIG. 7B and maintained in place by stabilizer 23d. By pressing the head 23e of the spacer plate 23c against the side of the CT table 20a and then locking the floor stand 23 in place, the floor stand is set to a pre-determined distance, indicated by "D" in FIG. 7B, from the side of the CT table 20a so that biopsies directly lateral to the patient can be performed. The spacing also allows the user room to manipulate needles without the laser guide being physically in the way. The base of the stand is preferably weighted to counterbalance the laser guide.

In either embodiment, table mount or floor mount, the horizontal rail 11 and vertical support post 15 are designed to be rigid. Rigidity is important as this fixes the right angle of the support rail 11 with respect to the vertical support post 15 and ensures the true horizontal position of the support arm 11. In so doing this ensures the accuracy of the angle achieved by the laser 1a as a result of the setting of the rotary stages 5 and 7 and the translational stage 9. Moreover, the tilt plate 16b ensures that the leveling of the horizontal rail 11 can be achieved without relying on the CT table 20a being level. Ultimate horizontal positioning is proven by a built in level indicating device 22 in the laser mounting plate 4, as previously discussed.

Alternatively, the horizontal rail 11 could be suspended from the ceiling, rather than being clamped to the vertical support post 15. In this embodiment, the horizontal arm could be mounted directly to the ceiling or adapters could be made to suspend the arm from IV holder tracks which already exist in the ceiling of most conventional CT scanner rooms.

The device is used as follows: First, the patient is placed onto the scanner table 20b in either the supine or prone position depending upon the part of anatomy to be localized (rarely the patient may also be placed in a decubitus position also). A scout or topogram scan may be obtained but is not crucial to the utilization of the device. The desired scans of the target site are then obtained.

Generally, prior to performing the scans, it is efficacious to first prepare the patients skin with sterile technique, e.g. with betadine, and then to put a sterile radiopaque grid, such as that disclosed in U.S. Pat. No. 4,916,715, or available from E-Z-EM of Westbury, N.Y. (EZ-Grid no. EG6500,) over the area to be biopsied. The edges of the sterile field are covered with sterile drapes and an additional sterile drape may be placed over the radiopaque grid if so desired to further protect the sterile field.

Depending upon anatomy, the CT scanner gantry 20c may be held in the straight axial position (i.e., 0°) or be tilted from true axial as much as 30 degrees. For example it is often useful to tilt the gantry 20c to avoid vital structures such as the lung bases (e.g., in adrenal gland biopsies).

After the relevant scans are obtained they are reviewed by the physician (generally a radiologist) and a needle path is chosen. The advantages of using the radiopaque grid, as discussed above, are that the grid will serve as an anatomic landmark on the patient and can be readily shown on the scans obtained prior to biopsy. Note that if it is elected to first scan the patient without the grid then it will often times be necessary to place a small radiopaque grid (e.g., easily prepared from several paper clips) on the patient's skin and then to obtain one or a few additional slices, and then after reviewing the scan to mark the patient's skin. The patient's skin at the needle entry site is generally infiltrated locally with 1% lidocaine and the patient is administered intravenous sedation as necessary (e.g., midazolam with morphine sulfate).

After reviewing the scans and choosing the appropriate level, the number and location of the entry site is chosen from the grid or the entry location may be drawn on the patient's skin when the grid is not used. A cursor is used to mark the entry site and the target site on the CRT monitor. The needle insertion depth and the angle of the path projected onto the x-z plane with respect to the z direction are then calculated by the computer and the needle path is displayed on the CRT monitor. If the desired path does not lie in the x-z plane (that is, the angle of the path when projected onto the y-z plane is not zero with respect to the z direction), then the gantry is typically rotated in the y-z plane to the desired angle of approach in the y-z plane. The gantry angle is then used as the beam angle in y-z plane. Alternatively, saggittal plane scans could be performed to determine the angle in the y-z plane during MRI procedures or reconstructions can be performed on spiral or helical CT scanners.

The rotary stage 5 is then set to the calculated angle in the x-z plane and the rotary stage 7 is set to the desired angle in the y-z plane. Since the rotary stages 7 and 5 are oriented so that they rotate in the y-z and x-z planes, respectively, no complex calculations are necessary to determine the angle settings for the device based on the output from the computer.

Next, the laser support structure 40 is moved into the approximate desired position by means of gross movement in the y direction by movement along the track 19, in the z direction by movement along the vertical post 15, and in the x direction along the horizontal rail 11, as previously discussed. Fine adjustment along the x and y directions is then achieved by use of the bi-directional translational stage 9 until the laser beam 35 strikes the patient's skin at the spot determined on the radiopaque grid or the mark drawn on the patient's skin.

A needle (such as a B-D spinal needle available from Becton Dickinson Co. of Franklin Lakes, N.J. or the probe according to the current invention, discussed below) is then placed such that the end of the needle touches the patient's skin at the same point as the laser beam. The hub of the needle is aligned such that the needle is now directly centered in the laser beam and therefore parallel to the laser beam as well. Using a free-hand technique, the needle is advanced into the patient to a predetermined depth while keeping the laser light centered onto the mid-point of the posterior surface of the needle's hub to ensure that the needle follows the desired path.

The symmetry of the device allows for mounting on either side of the CT table, and the horizontal support arm 11 can be rotated parallel to the table for easier access during awkward biopsies.

For use in CT, the components of the device, especially stages 5, 7, 9, the horizontal arm 11, and the support post 15, are preferably made of light weight steel or aluminum. Alternatively, the components may be made of fiberglass, carbon fiber, or composite plastics such as delrin. In general the material is selected to be as light as possible while still providing the necessary rigidity. Different components may be made of different materials. For example the horizontal arm 11, stages 5, 7, 9, and brackets 6 and 8 may be made of aluminum and the vertical post 15 made of steel. The floor stand 23 may be made of steel or aluminum and the wheels 23a may be made of rubber or plastic.

For use in MR, the device should be made of MR compatible materials and the use of ferromagnetic materials should be avoided. Preferred materials for constructing the device would include high nickel steel, aluminum, carbon fiber and fiber glass. When the device is used with MR instead of a radiopaque grid, an MR visible grid may be placed on the patients skin prior to scanning. Such a grid may be prepared from materials containing fluorinated compounds, iron oxides, oily materials, aqueous solutions containing paramagnetic salts (e.g., gadolinium salts or chelates) or other such materials that are visible on MRI. After obtaining localizing images similar to that described above the needle path is drawn on the CRT monitor and the needle is placed similar to that described above with CT.

In order to use the device of the current invention, the operator must grasp the hub of a standard needle such that his or her fingers do not obscure the back of the needle hub. A probe adapted for use in conjunction with the device is shown in FIGS. 8–14.

To facilitate holding the needle hub when the device is used, the probe is fitted with a flared flange on the hub. This new flanged hub 25a incorporates an innovative locking stylet design 25k which also facilitates gripping the needle by the operator's fingers such that the fingers do not obscure the backside of the needle hub where the laser beam strikes.

Figure 8:
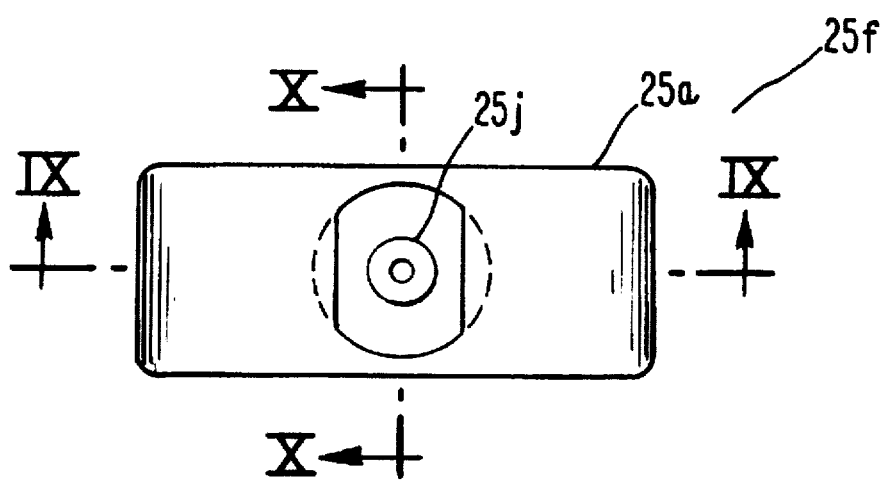
FIG. 8 is plan view of the needle portion of a biopsy probe for use with the device shown in FIG. 1B.
Figure 9:
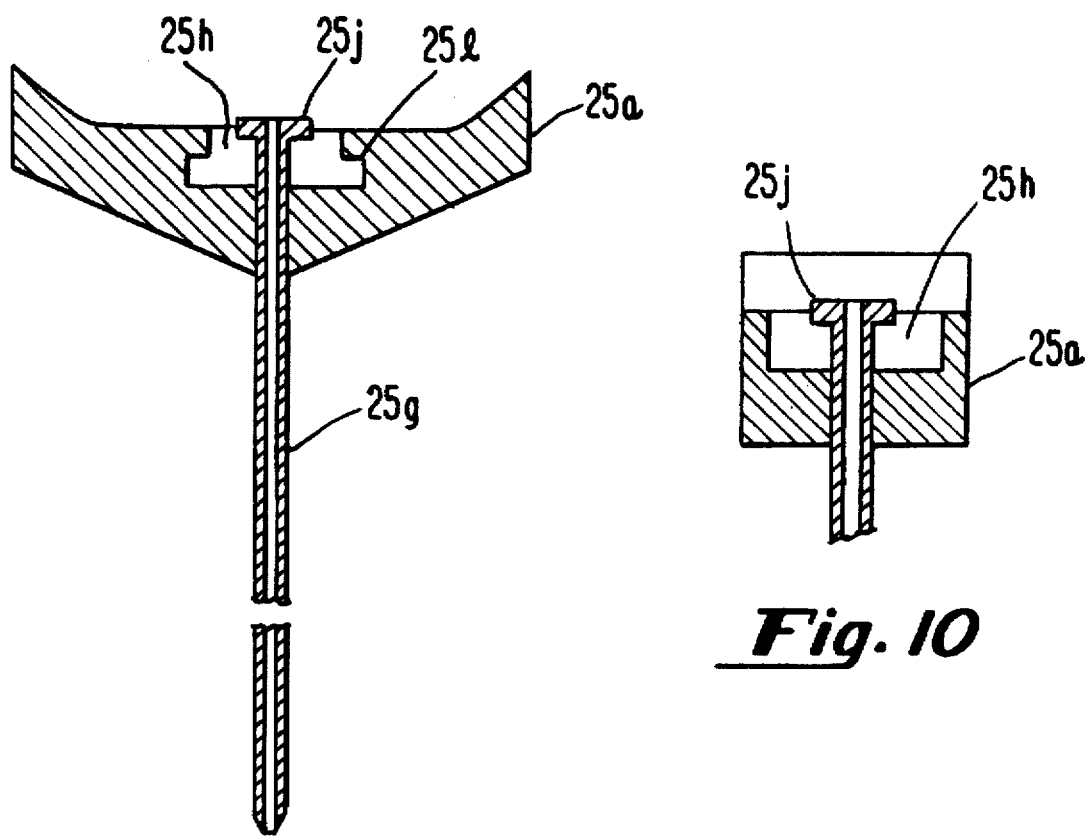
FIG. 9 is a cross-section of the needle taken along line IX—IX shown in FIG. 8.
Figure 10:
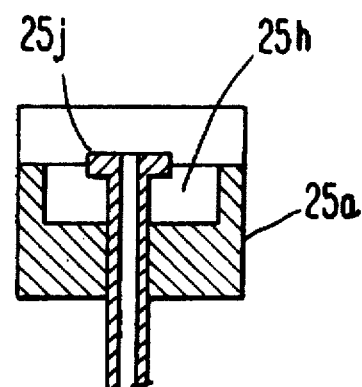
FIG. 10 is a cross-section of the needle taken along line X—X shown in FIG. 8.

As shown in FIGS. 8–10, the needle portion 25f of the probe is comprised of a flanged hub 25a that is fixed to a hollow needle shaft 25g. The needle shaft 25g preferably has a beveled end, as shown in FIG. 9. A chamber is formed in the hub 25a so that the shaft 25g extends through the chamber and the flange 25j is disposed within the chamber. The chamber has a circular enlarged bottom portion 25l and a narrow, approximately rectangular throat portion 25h disposed above the bottom portion 25l.

Figure 11:
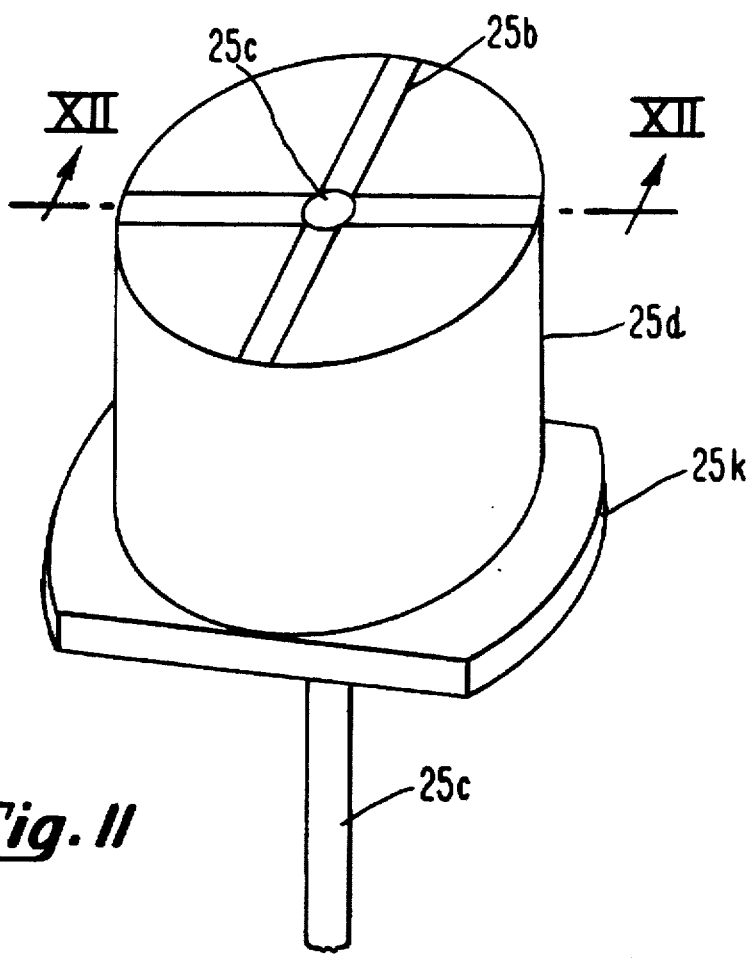
FIG. 11 is an isometric view of the upper portion of a locking stylet for use in the needle shown in FIG. 8.
Figure 12:
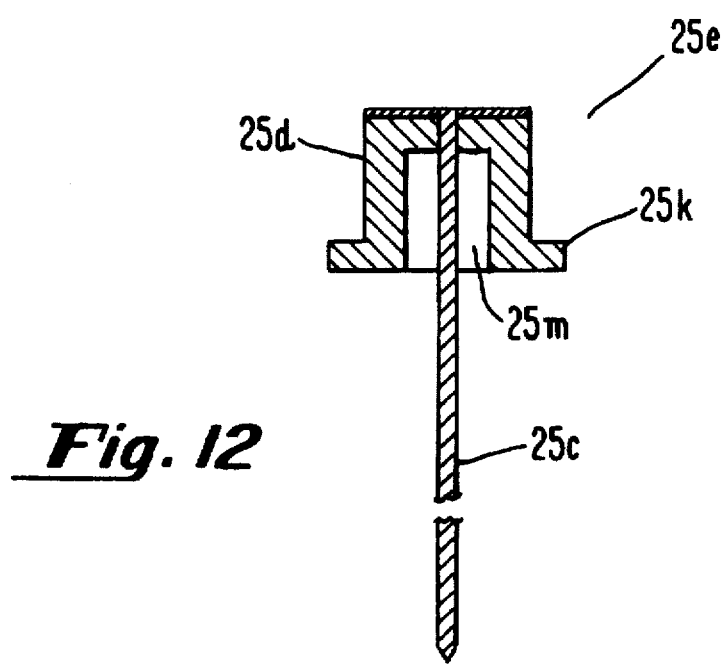
FIG. 12 is a cross-section of the stylet shown in FIG. 11 taken along line XII—XII shown in FIG. 11.

As shown in FIGS. 11 and 12, the stylet portion 25e of the probe has a shaft 25c with, preferably, a conical point at its distal end and a locking cylinder 25d affixed to its proximal end. The locking cylinder 25d has a flange 25k that projects outwardly from the cylinder around a portion of its circumference. A cavity 25m is formed within the locking cylinder 25d. A device that facilitates aiming the laser beam onto the probe, such a cross hairs 25b, are formed on the top of the locking cylinder 25d, as shown in FIG. 11.

Figure 13:
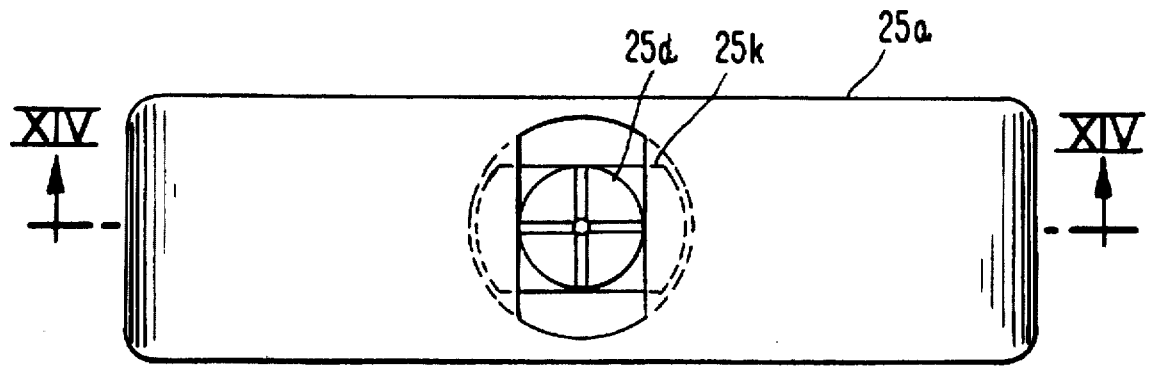
FIG. 13 is a plan view of the assembled biopsy probe according to the current invention.
Figure 14:
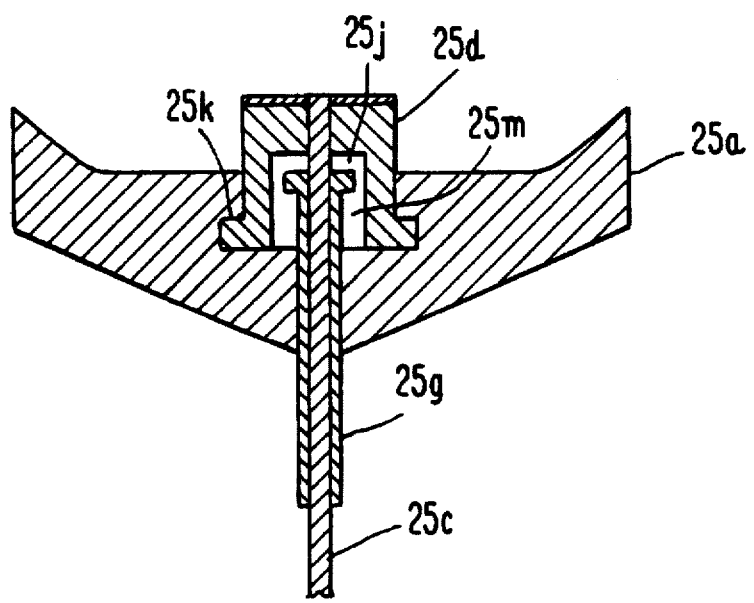
FIG. 14 is a cross-section of the biopsy probe taken along line XIV—XIV shown in FIG. 13.

To assemble the probe, the stylet shaft 25c is slid into the hollow needle shaft 25g with the locking cylinder flange 25k oriented so that it is aligned with the throat 25h in the flange 25a—that is, the cylinder 25k is rotated until the flange 25k is oriented so that it extends across the width of the flange 25a when viewed in FIG. 8. When the locking cylinder flange 25k has been seated inside the bottom portion 25l of the chamber, the locking cylinder 25d is then rotated 90° so that it extends along the length of the flange 25a as shown in FIGS. 13 and 14. This causes the stylet 25e to be locked into position on the needle 25f, with the needle flange 25j disposed within the cavity 25m, as shown in FIG. 14.

To unlock and remove stylet 25e, the locking cylinder 25d is simply rotated 90° again while holding the flared needle hub 25a still.

The probe facilitates holding the needle while the laser beam strikes the dead center in the cross hairs 25b on the posterior surface of the needle hub 25a and subsequently facilitates directing the needle to its intended target. With conventional needles, when force is applied to the needle by pushing on the end of the hub the needles, which are thin, frequently bow. Moreover, covering the hub end with one's finger to prevent the stylet from sliding out of the needle obscures visualization of the laser beam on the hub.

The flanged hub with locking stylet according to the current invention helps probe placement in four ways: (1) it allows greater force to be applied against resistant tissues, (2) it gives more balanced pressure load along the axis of the needle which decreases needle flexion during higher force biopsy attempts (i.e.. through scar tissue or bone), (3) it gives a firm finger hold for biopsy control while not obscuring the hub end during laser guidance, and (4) it prevents the stylet from inadvertently releasing during more forceful biopsies alleviating the need to generate force by placing one's finger over the hub end as required with previous conventional needles.

For CT, the probe may be made of conventional materials. For MRI high nickel steel may be used, aluminum or other non-ferromagnetic materials. Preferably the stylet tip's point is sharp and conical shaped, similar to a pin point, rather than beveled like conventional needles, since angle beveled needle tips make it more difficult to pass the needle straight within the patient's tissues.

Figure 15:
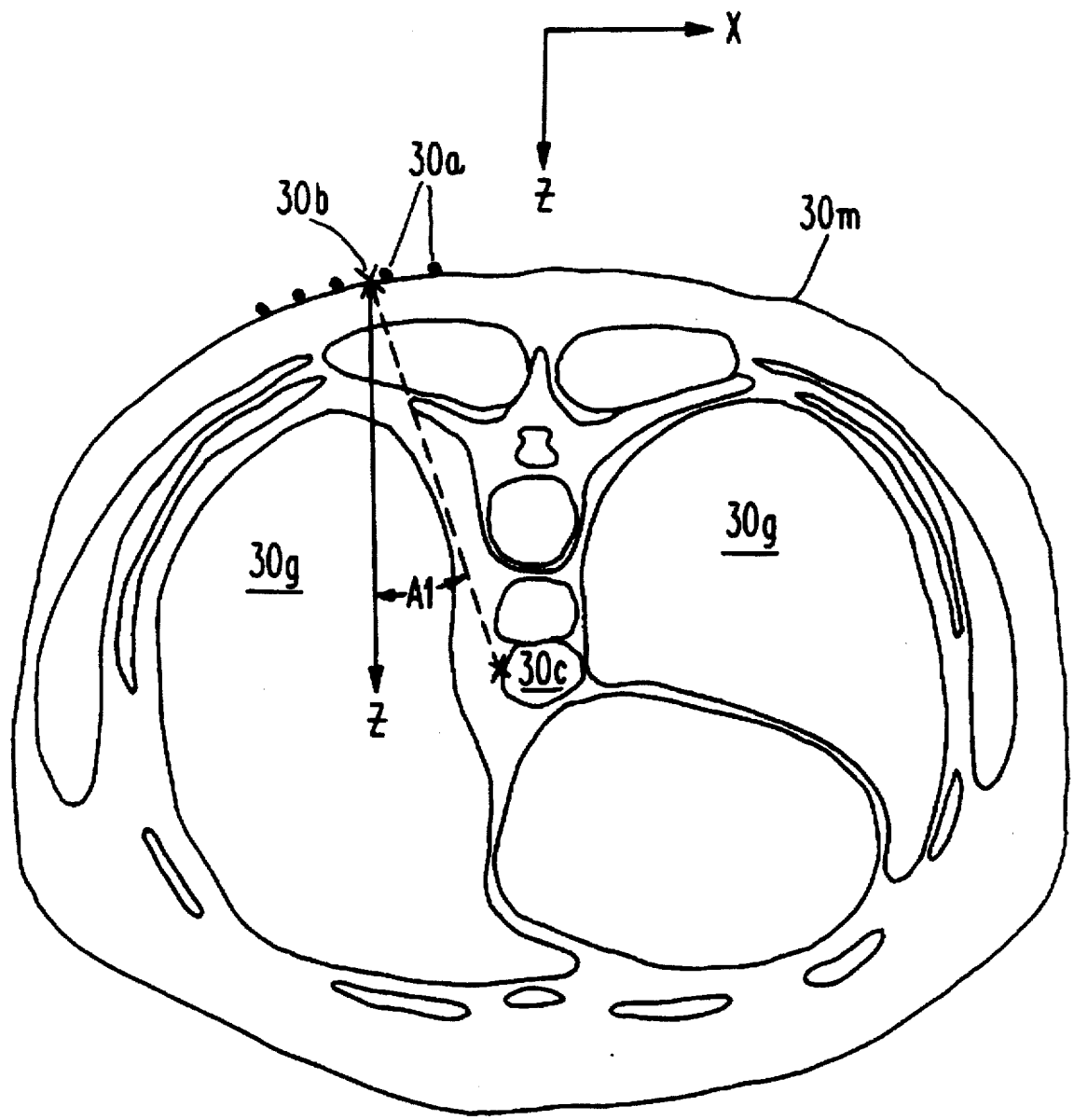
FIG. 15 is a schematic diagram of a CT typical image taken during a biopsy procedure.

The following actual case example is meant to illustrate the use of the laser beam directing and supporting device, with reference to the scan shown in FIG. 15.

A 60 year old woman with a history suggesting occult malignancy and an esophageal stricture presented for biopsy of an esophageal mass 30c adjacent to the aorta 30d. The gastroenterologist could not see the mass from within the esophagus and when he attempted biopsy by endoscopy, the results were negative. Therefore the patient was referred for CT guided biopsy. Most physicians would not attempt this biopsy as the accuracy needed to hit the lesion exceeds freehand guided accuracy. The only path to the lesion has approximately 1 millimeter margin for error between the needle path and the aorta 30d on one side and the lung 30g on the other side, both vital structures.

The patient was positioned prone and scanned by the CT scanner made by Siemens DRH of Iselin, N.J. A suitable scan slice was chosen and localization grid 30a was placed on the overlying skin 30m. The biopsy entry path 30b was plotted on the CRT and the skin entrance site was marked. The biopsy depth and angle were automatically provided by the computer of the CT scanner. In this case, the x-z plane angle was determined to be A1=−20° with respect to the z direction and the y-z plane angle was selected to be zero or parallel to the CT gantry (A2=0°).

The patient was re-scanned after local anesthesia was infiltrated at the skin entrance site to confirm correct biopsy path angles and distance (A1=−20°, Distance=12.5 centimeters). The rotary stage 5 was set at −20° and the rotary stage 7 was set at 0°. The laser beam support structure 40 was then moved to position along the track 19 and the horizontal rail 11 and then its position was finely adjusted using the bi-directional stage 9 until the laser beam shown directly on the skin entry mark 30b. The needle was advanced with twisting motion like a drill through the skin entry point 30b along the path of laser light to the predetermined depth. Re-scan confirmed exact needle placement. This particular biopsy was performed twice and confirmed exact desired needle placement was seen on both passes. The aorta 30d and lung 30g were avoided in a biopsy that was not only more accurate but faster than freehand technique.

Laser guidance with the device according to the current invention is much faster than conventional biopsies because the need for repositioning the needle during biopsy attempts is essentially eliminated.

The device of the current invention may be automated and computer controlled. As the needle entry site and path are calculated on the CRT monitor the laser can be controlled by interfacing the software of the CT scanner or a work station to the laser guidance device. The automated device may then be moved under computerized control rather than manually as in the above examples.

Computerized control of the device will be quite helpful for cases in which multiple probes are placed into the patient. For cases in which only one or a couple of entry sites are selected, e.g. most biopsies, manual control is preferred. Indeed it is cheaper to provide the device equipped for manual usage as this is cheaper and suitable for most applications. The computerized version of the device is preferred for applications where multiple needles or probes might be used to treat a patient, e.g. in interstial radiotherapy.

The present invention may be embodied in other specific forms without departing from the spirit or essential attributes thereof and, accordingly, reference should be made to the appended claims, rather than to the foregoing specification, as indicating the scope of the invention.

What is claimed:

1. An apparatus for performing light beam guided penetrations of a patient's body, comprising:
 a) a vertically extending post;
 b) a rail projecting from said post in a first horizontally extending direction;
 c) a support structure slidably mounted on said rail for movement therealong in said first horizontal direction, a first rotatable mount coupled to said support structure, a second rotatable mount, means for coupling said first rotatable mount to said second rotable mount so as to prevent translational motion therebetween, said first and second rotatable mounts oriented so as to provide rotation within first and second perpendicularly oriented planes, respectively, said first plane being substantially vertically oriented; and
 d) a light source coupled to said second rotatable mount for projecting a beam of light onto said patient.

2. The apparatus according to claim 1, wherein said first plane is parallel to a sagittal plane of said patient.

3. The apparatus according to claim 1, wherein said first and second rotatable mounts are each comprised of first and second members, said second members being rotatably coupled to said first members.

4. The apparatus according to claim 3, wherein said support structure comprises a first bracket having a first support plate, said first member of said first rotatable mount being attached to said first support plate.

5. The apparatus according to claim 4, wherein said first support plate extends in a substantially vertical plane.

6. The apparatus according to claim 5, further comprising a second bracket mounted on said second member of said first rotatable mount, whereby said second bracket rotates relative to said first member of said first rotatable mount and relative to said first bracket and does so in a plane parallel to said first plane.

7. The apparatus according to claim 6, wherein said first member of said second rotatable mount is attached to said second bracket, whereby said second rotatable mount rotates along with said second bracket.

8. The apparatus according to claim 7, wherein said second bracket comprises a second support plate, said first member of said second rotatable mount attached to said second support plate, said light beam source attached to said second member of said second rotatable mount, whereby said light source rotates along with said second member of said second rotatable mount.

9. The apparatus according to claim 8, wherein said second member of said first rotatable mount rotates with respect to said first member of said first rotatable mount around an approximately horizontally extending axis, said second support plate extending parallel to said axis, whereby said second support plate rotates in a plane parallel to said first plane.

10. The apparatus according to claim 1, further comprising means for rotating said rail around said post.

11. The apparatus according to claim 10, wherein said means for rotating said rail comprises means for rotating said rail within an approximately horizontally extending plane.

12. The apparatus according to claim 1, wherein said rail is slidably mounted on said post.

13. The apparatus according to claim 1, further comprising means for adjusting the orientation of said post with respect to the vertical direction.

14. The apparatus according to claim 1, further comprising a track extending in a second direction substantially perpendicular to said first direction, and wherein said vertically extending post is slidably mounted on said track for movement therealong in said second direction.

15. An apparatus for directing a light beam toward a patient's body, comprising:
   a) an approximately horizontally extending rail;
   b) a first bracket having a base plate and an approximately vertically extending support plate;
   c) means for slidably mounting said base plate of said first bracket onto said rail;
   d) first rotatable mounting means attached to said support plate of said first bracket;
   e) a second bracket having an approximately vertically extending base plate and a support plate, said base plate of said second bracket attached to said first rotatable mounting means;
   f) second rotatable mounting means attached to said support plate of said second bracket, whereby said first and second rotatable mounting means are capable of translation only as a unit; and
   g) means for generating a beam of light, and means for attaching said light beam generating means to said second rotatable mounting means.

16. The apparatus according to claim 1, further comprising:
   a) first coarse adjusting means for coarsely adjusting the position of said support structure in said first horizontal direction; and
   b) first fine adjusting means for finely adjusting the position of said support structure in said first horizontal direction.

17. An apparatus for generating a beam of light for use in guiding the entry of a probe into a patient's body with reference to an orthogonal x-y-z coordinate system in which the z-direction is approximately vertical and the x- and y-directions are approximately horizontal so that the x-z and y-z planes extend substantially vertically, comprising:
   a) means for generating a beam of light;
   b) a rail having means for being oriented so as to extend over said patient's body in a first horizontal direction;
   c) a support structure slidably suspended from said rail for movement in said first horizontal direction; and
   d) means for directing said beam of light in a direction that forms a compound angle with respect to said z-direction, said compound angle forming first and second acute angles with respect to said z-direction in y-z and x-z planes, respectively, said light beam directing means mounted on said support structure and comprising (i) first rotating means for rotating said light beam generating means in said y-z vertical plane so as to form said first acute angle with respect to said z-direction in said y-z plane, and (ii) second rotating means for rotating said light beam generating means in said x-z vertical plane so as to form said second acute angle with respect to said z-direction in said x-z plane;
   e) a mounting block secured to said second rotating means, said light beam generating means being attached to said mounting block; and
   f) means for indicating the orientation of said light beam generating means with respect to said z-direction, said orientation indicating means attached to said mounting block.

18. The apparatus according to claim 15, wherein said means for attaching said light beam generating means to said second rotatable mounting means comprises a mounting block secured to said second rotatable mounting means, said light beam generating means being attached to said mounting block, and further comprising means for indicating the orientation of said light beam generating means with respect to the vertical direction, said orientation indicating means also being attached to said mounting block.

* * * * *

UNITED STATES PATENT AND TRADEMARK OFFICE
CERTIFICATE OF CORRECTION

PATENT NO. : 5,628,327
DATED : May 13, 1997
INVENTOR(S) : Unger et al.

It is certified that error appears in the above-identified patent and that said Letters Patent is hereby corrected as shown below:

In column 3, line 18, please delete "elevations" and insert --elevation-- therefor.

In column 3, line 51, please delete "sagital" and insert --sagittal-- therefor.

In column 4, line 15, please delete "A shown" and insert --As shown-- therefor.

In column 7, line 18, please delete "saggittal" and insert --sagittal-- therefor.

In column 8, line 42, please delete "such a" and insert --such as-- therefor.

In column 10, line 14, please delete "interstial" and insert -- interstitial-- therefor.

Signed and Sealed this

Ninth Day of September, 1997

Attest:

Attesting Officer

BRUCE LEHMAN

Commissioner of Patents and Trademarks